(12) United States Patent
Griffiths et al.

(10) Patent No.: US 10,919,925 B2
(45) Date of Patent: *Feb. 16, 2021

(54) LIQUID COMPOSITION FOR RECONSTITUTING PRESSED POWDER COSMETICS

(71) Applicants: Tess Griffiths, Los Angeles, CA (US); Barbara Villegas, Los Angeles, CA (US)

(72) Inventors: Tess Griffiths, Los Angeles, CA (US); Barbara Villegas, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/606,802

(22) Filed: May 26, 2017

(65) Prior Publication Data

US 2018/0339005 A1 Nov. 29, 2018

(51) Int. Cl.
| | | |
|---|---|---|
| *A61K 36/18* | (2006.01) | |
| *A61K 36/35* | (2006.01) | |
| *A61K 36/889* | (2006.01) | |
| *A61K 8/34* | (2006.01) | |
| *A61K 8/67* | (2006.01) | |
| *C07H 3/02* | (2006.01) | |
| *A61K 36/53* | (2006.01) | |
| *A61K 36/185* | (2006.01) | |
| *A61K 8/9794* | (2017.01) | |
| *A61Q 1/12* | (2006.01) | |
| *A61K 8/02* | (2006.01) | |
| *A61K 8/9789* | (2017.01) | |

(52) U.S. Cl.
CPC .............. *C07H 3/02* (2013.01); *A61K 8/022* (2013.01); *A61K 8/34* (2013.01); *A61K 8/678* (2013.01); *A61K 8/9789* (2017.08); *A61K 8/9794* (2017.08); *A61K 36/185* (2013.01); *A61K 36/53* (2013.01); *A61K 36/889* (2013.01); *A61Q 1/12* (2013.01)

(58) Field of Classification Search
CPC .......... A61K 36/18; A61K 8/34; A61K 8/678; A61K 36/53; A61K 36/889
See application file for complete search history.

(56) References Cited

U.S. PATENT DOCUMENTS

| | | | |
|---|---|---|---|
| 6,257,247 B1* | 7/2001 | Benzinger | A61K 8/97 132/200 |
| 2002/0044977 A1* | 4/2002 | Close | A61K 8/0212 424/725 |
| 2008/0219938 A1* | 9/2008 | Grune | A61K 8/25 424/59 |
| 2014/0065196 A1* | 3/2014 | Gabbay | A61Q 19/08 424/401 |
| 2015/0238409 A1* | 8/2015 | Eizen | A61K 8/922 424/602 |
| 2015/0252291 A1* | 9/2015 | Levine | A61L 9/013 512/2 |
| 2017/0065515 A1* | 3/2017 | Karam | A61K 8/97 |

OTHER PUBLICATIONS

United Descaler (2014). "Decyl glucoside". Retrieved on Jun. 15, 2018. Retrieved from in the internet <URL: https://www.ceramiracle.com/blogs/decyl-glucoside/decyl-glucoside>.*

* cited by examiner

*Primary Examiner* — Doan T Phan
(74) *Attorney, Agent, or Firm* — Eric Kelly

(57) ABSTRACT

A liquid composition is provided which can be applied to broken fragments of a pressed powder cosmetic in order to recombine or reconstitute such fragments in their original packaging. This avoids wasting broken cosmetic fragments and further allows a consumer to use the reconstituted cosmetic for its original purpose.

2 Claims, No Drawings

LIQUID COMPOSITION FOR RECONSTITUTING PRESSED POWDER COSMETICS

GOVERNMENT CONTRACT

Not applicable.

CROSS-REFERENCE TO RELATED APPLICATIONS

Not applicable.

Statement Re. Federally Sponsored Research/Development

Not applicable.

Copyright & Trademark Notices

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to cosmetics preparations and, more particularly, to compositions for reconstituting powder-based, compact, and even pressed cosmetics.

BACKGROUND

Many people use cosmetics recreationally and professionally to augment and even sometimes change their appearance. As a result, there are countless varieties of cosmetics available in the marketplace, including cosmetics comprising powdered compositions pressed into and further stored in shallow pans. Though common, collections of cosmetics can be relatively expensive to acquire and maintain. In some instances, desirable ingredients and/or brand recognition may increase the cost of these cosmetics. Some compositions may be pressed in to aesthetic, vanity packaging in an effort to provide cosmetics fit for display. Additionally, many cosmetics are configured to serve individual purposes. That is, cosmetic foundation known in the art, for example, is not typically formulated to also serve as eyeshadow or blush, and vice versa. This requires consumers to buy various types of cosmetics, in a variety of shades when desired, to complete her entire beauty regimen.

Of course, regardless of cost, cosmetic compositions are rarely, if ever, immune from damage. For example, pressed powder cosmetics arranged in pans and resealable casings have been known to shatter, become undesirably fragmented, or otherwise become loosened when dropped or struck. This damage can make the cosmetic difficult to use. For example, applying a makeup brush or other implement to a broken powder cosmetic may cause a user to draw too much of the cosmetic product onto their implement. This may negatively affect application of the product on the skin. As just one example of a result, a user may inadvertently apply too much of the cosmetic to their face, which may cause their appearance to be unintentionally blotchy or overly pigmented. In some cases, fragmented portions of a pressed powder cosmetic may even fall entirely out of its pan, making a mess of nearby surfaces and contaminating the fallen portions. This may render the powder unusable and lower the shelf-life of the original product.

Some solutions have been proposed to solve the problem of broken pressed powder cosmetics. One exemplary proposal has been to repurpose the broken pieces of pressed powder cosmetics. For instance, compacted powder blush, typically marketed for application to the cheeks as a rouge, may be made into a creamy gloss or balm by mixing crushed pieces with some amount of petroleum jelly or emollient compositions. The same may be done for pressed powder eyeshadows. This can be a beneficially frugal way of avoiding waste, however, it is obviously deficient for the fact that a consumer may no longer use the original cosmetic in the manner it was prescribed.

Some solutions have been proposed to reconstitute and therefore prolong the life of a shattered compact makeup in its original form. For instance, some knowledgeable in the art recommend fully removing broken pressed powder from its pan, crushing it further, then mixing the crushed cosmetic with rubbing alcohol, vodka, or surgical spirits. Once mixed, a paste like slurry can be returned to and smoothed in the pan. Then, the slurry may be left exposed to the air so that any liquid may evaporate, leaving behind a reconstituted, pressed powder cosmetic. Related teachings may be seen in U.S. Pat. No. 1,968,475 to Beckwith et al. and U.S. Pat. Pub. No. 2012/0286441 filed by Johnson.

These proposals have a variety of deficiencies. For instance, although various alcohols have been known to imbue certain cosmetic products with a desirable, quick-drying finish, minimizing amounts of alcohol in cosmetic preparations may be preferable for many consumers, especially those with sensitive skin. Indeed, alcohols can be damaging and irritating to the skin, some may cause skin cell death, they may damagingly remove barrier lipids, and even exacerbate acne. In addition, rubbing alcohol and other surgical spirits are known to have a particularly unpleasant smell which many consumers may prefer to avoid.

Another proposal to solve the problem of wasting broken pressed powder cosmetics has been to recompact the fragments together in the shallow pan by applying, variously, heat and pressure to the fragments. Of course, applications of heat may be dangerous to the consumer and may further, undesirably, melt or burn ingredients comprising the cosmetic. Forcibly reconstituting the pressed powder may cause damage to the storage pan and/or case and may not sufficiently bind the loosened fragments.

Although proposals for using and repairing broken cosmetic fragments have been suggested, all of those heretofore known suffer from a number of disadvantages. As such, there remains a need for a composition for reconstituting pressed powder cosmetics so that they may be useable in their original form and packaging.

SUMMARY

The present disclosure is directed to a composition for repairing broken or fragmented pressed powder cosmetics. In particular, the composition reduces amounts of alcohol sometimes applied to such ends. Additionally, the composition may be applied to fragmented cosmetic powders while avoiding any need to remove such powder from its pan or original casing. Indeed, the composition may even avoid a need to break pressed powders into smaller fragments prior to reconstitution.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the composition comprises only about 10% to about 30% by weight of alcohol, such as ethanol, grain alcohol, or even isopropyl alcohol. Alcohol may be beneficial as a volatile liquid that readily evaporates at normal temperatures and even further comprises anti-bacterial properties. Thus, when applied to pressed powder cosmetics, it may effectively kill bacteria which may have become mixed in cosmetic particles and further evaporate from any mixture to provide a reconstituted pressed powder. However, as noted above, use of alcohol alone involves a variety of deficiencies. Therefore, in order to avoid an overabundance of alcohol, *Hamamelis virginiana*, more commonly known as witch hazel, may be provided in amounts from about 70% to about 90% of the composition by weight.

Witch hazel may comprise tannins, volatile oils, humectants, antioxidants, and anti-bacterial, anti-fungal, and anti-inflammatory properties as its primary active ingredients, which contribute to its astringent and other benefits. The ability of witch hazel to shrink or contract tissues, such as skin, may make its application in the field of cosmetics particularly desirous. Anti-fungal properties in particular may be desirous in preventing fungal growths from forming in reconstituted pressed powders.

Additionally, a foaming agent, wetting agent, or even surfactant may be provided in order to reduce the surface tension of liquids in the composition. In some embodiments, a surfactant may be provided as decyl glucoside in an amount of about 0.5% to about 5% of the composition by weight. Including a surfactant as an element comprising the composition may configure the composition to break up residual oils in fragmented pressed powders and allow the pieces to be more evenly recombined. Additionally, including a foaming and/or wetting agent and surfactant may configure the composition for convenient dispensation from a foaming dispenser. Decyl glucoside may be particularly desirable for this purpose due to the fact that it is relatively mild, plant-based, and even biodegradable. Of course, other surfactants are known to those skilled in the art and may be used in combination with or instead of decyl glucoside. Thus, the foregoing is offered by way of example only and not limitation.

In some embodiments, the composition may be applied to cosmetics in the following manner. Salvagable fragments, including any loosened powder particles, of a pressed powder cosmetic may be gathered and swept into any pan or other packaging provided with the cosmetic. These salvageable fragments and any loose powder may be pressed into the pan using a finger or other convenient implement. The liquid composition for reconstituting pressed powder cosmetics may be dispensed over the entire area of the fragmented, but gathered, cosmetic. In some embodiments, the composition may be dispensed from a foaming container so that the composition may be applied as a vast plurality of small bubbles all over the cosmetic. Once the foamed embodiment of the liquid composition dissolves, it may be seen that the gathered cosmetic may take on the texture of a paste-like substance. Such paste-like substance may be smoothed and again pressed by hand or by other implement in the pan. Then, the paste-like cosmetic may be left in a well-ventilated area for about 6 to about 24 hours so that the liquid composition, now mixed with the cosmetic, may evaporate and leave behind a relatively dry, reconstituted, pressed powder cosmetic. Other steps may be practiced to provide the reconstituted cosmetic with a desirable aesthetic appearance.

Additional beneficial ingredients may be provided in smaller amounts, in combinations comprising about 0.01% to about 10% by weight of the composition. For instance, in some embodiments, a pleasantly scented volatile oil, also known as an essential oil, may comprise the invention to improve any smell associated with the composition. As an example, in some embodiments, lavender oil may comprise about 0.01% to about 0.2% of the composition by weight. Of course, other pleasantly scented essential oils are known in the art and may be used instead or in addition to lavender oil. Additional carrier oils may be provided, such as jojoba oil and fractionated coconut oil, either alone or in combination with one another in amounts of about 0.01% to about 0.2% of the composition by weight, to prevent the essential oil from evaporating entirely from the reconstituted pressed powder. This may ensure that even once dried, the pressed powder retains the pleasant scent of the volatile or essential oil. These, along with the essential oils may be provided in small amounts relative to the total weight of the composition so that general wetness of the reconstituted pressed powder is avoided.

Vitamins and other minerals may be included in the liquid composition as well. For instance, it may be desirable to include vitamin E in amounts of about 0.01% to about 0.2% of the composition by weight may also be provided as an additional ingredient in small amounts due to its anti-inflammatory, anti-oxidant, and UV protecting qualities.

One or more of the above-disclosed embodiments, in addition to certain alternatives, are provided in further detail below with reference to the attached figures. The disclosed subject matter is not, however, limited to any particular embodiment disclosed.

Several advantages of one or more aspects are to provide a pressed powder cosmetic repair formula that:
  (a) reduces amounts of harsh alcohols and other chemicals of known solutions;
  (b) comprises beneficial and/or natural ingredients;
  (c) minimizes foul odors;
  (d) comprises pleasant odors;
  (e) comprises anti-fungal ingredients;
  (f) may be effectively applied to cosmetic powder fragments in their original cosmetic pan and/or packaging;
  (g) avoids necessarily further breaking or fragmenting pressed powders prior to reconstitution.

These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus the scope of the embodiments should be determined by the claims that the appended and their legal equivalents, rather than by the examples given.

The description of the invention which follows, together with the accompanying examples should not be construed as limiting the invention to the examples shown and described, because those skilled in the art to which this invention pertains will be able to devise other forms thereof within the ambit of the appended claims.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments. One skilled in the art will understand that the invention may be practiced without such details. In such instances, well-known structures and functions have not been shown or described in detail to avoid unnecessarily obscuring the description of the embodiments.

The preferred embodiment of a formulation for repairing and reconstituting fragmented or otherwise broken portions of pressed powder cosmetics allows a consumer to do so in the cosmetic's original casing while avoiding a need to entirely crush or remove the cosmetic. Applicant's liquid composition reduces amounts of alcohol previously used to affect such results and comprises additional beneficial ingredients.

Ingredients comprising the liquid composition for reconstituting pressed powder cosmetics may be mixed in any amount so long as some time after application to the broken cosmetic powder, or about 6 to about 24 hours, such reconstituted powder will be relatively dry to the touch and may be applied by a consumer as a pressed powder cosmetic.

More particularly, the composition may comprise witch hazel in combination with a volatile liquid, and a wetting agent for reducing surface tension in the composition. The wetting agent, or surfactant, may cause the liquid composition to be dispensable as a foam. In some embodiments, the volatile liquid is an alcohol provided in an amount up to about 30% by weight of the composition. In some embodiments, the wetting agent is decyl glucoside.

Additionally the composition may comprise additional ingredients such as fragrance, a carrier oil for the fragrance and even vitamins and/or minerals.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

Examples of the Preffered Embodiment of the Composition

In order to more fully teach what the Applicant regards as his invention, the following example is given. It should be understood that the formulations set forth in the Example is not to be construed as limiting of the scope of the invention, except so far as they yield natural toothpaste having the desired properties and characteristics.

Formulations for repairing or reconstituting fragmented or otherwise broken pressed powder cosmetics have been proposed in the past. More particularly, and by way of example, the following chart illustrates a formulation of the same with the percentages given by weight of the formula.

Example 1

| Ingredient | Percentage |
|---|---|
| Isopropyl alcohol | 70.00 |
| Water | 30.00 |
| TOTAL: | 100.00% |

The following ingredients are an example of Applicant's invention with the percentages being given by weight of its liquid:

| Ingredient | Percentage |
|---|---|
| *Hamamelis virginiana* | 84.44 |
| Grain alcohol | 13.74 |
| Decyl glucoside | 1.57 |
| Lavendar essential oil | 0.10 |
| Jojoba oil | 0.05 |
| Fractionated coconut oil | 0.05 |
| Vitamin E | 0.05 |
| TOTAL: | 100.00% |

Conclusions, Ramifications, and Scope

While certain embodiments of the invention have been illustrated and described, various modifications are contemplated and can be made without departing from the spirit and scope of the invention. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the liquid composition for reconstituting pressed powder cosmetics with which that terminology is associated. In general, the terms used in the following claims should not be constructed to limit the liquid composition for reconstituting pressed powder cosmetics to the specific embodiments disclosed in the specification unless the above description section explicitly define such terms. Accordingly, the actual scope encompasses not only the disclosed embodiments, but also all equivalent ways of practicing or implementing the disclosed invention. The above description of embodiments of the liquid composition for reconstituting pressed powder cosmetics is not intended to be exhaustive or limited to the precise form disclosed above or to a particular field of usage.

While specific embodiments of, and examples for, the composition are described above for illustrative purposes, various equivalent modifications are possible for which those skilled in the relevant art will recognize.

While certain aspects of the invention disclosed are presented below in particular claim forms, various aspects of the method, system, and apparatus are contemplated in any number of claim forms. Thus, the inventor reserves the right to add additional claims after filing the application to pursue such additional claim forms for other aspects of the liquid composition for reconstituting pressed powder cosmetics.

What is claimed is:

1. A composition for reconstituting loosened compact cosmetic powders, comprising:
   - 84.44 wt. % *Hamamelis virginiana*;
   - 13.7 wt. isopropyl alcohol;
   - 1.57 wt. % decyl glucoside;
   - 0.10 wt. % lavender essential oil;
   - 0.05 wt. % jojoba oil;
   - 0.05 wt. % fractionated coconut oil; and
   - 0.05 wt. % vitamin E.

2. The composition according to claim 1, wherein the composition further comprises one or more minerals.

* * * * *